US007723301B2

(12) United States Patent
Shaughnessy et al.

(10) Patent No.: US 7,723,301 B2
(45) Date of Patent: May 25, 2010

(54) PHARMACEUTICAL COMPOSITIONS COMPRISING AN ANTI-TERATOGENIC COMPOUND AND APPLICATIONS OF THE SAME

(75) Inventors: John D. Shaughnessy, Little Rock, AR (US); Uli Ruther, Dusseldorf (DE); Jurgen Knobloch, Cologne (DE)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 202 days.

(21) Appl. No.: 11/846,854

(22) Filed: Aug. 29, 2007

(65) Prior Publication Data

US 2009/0060903 A1 Mar. 5, 2009

(51) Int. Cl.
*A61K 38/00* (2006.01)
(52) U.S. Cl. ...................... 514/12; 424/130.1
(58) Field of Classification Search ........................ None
See application file for complete search history.

(56) References Cited

U.S. PATENT DOCUMENTS

| | | | |
|---|---|---|---|
| 6,914,067 | B2 | 7/2005 | Govindarajan et al. |
| 2003/0068673 | A1 | 4/2003 | Tall et al. |
| 2004/0038860 | A1 | 2/2004 | Allen et al. |
| 2004/0267000 | A1 | 12/2004 | Tall et al. |
| 2005/0079159 | A1* | 4/2005 | Shastri et al. ............... 424/93.7 |
| 2005/0203060 | A1 | 9/2005 | Govindarajan et al. |
| 2005/0282192 | A1* | 12/2005 | Shaughnessy et al. ........... 435/6 |
| 2006/0030042 | A1* | 2/2006 | Brivanlou et al. ............ 435/366 |
| 2006/0211728 | A1* | 9/2006 | Greig et al. .................. 514/300 |
| 2006/0286584 | A1 | 12/2006 | Duojia |
| 2007/0032453 | A1* | 2/2007 | Towner et al. ................. 514/62 |
| 2009/0142337 | A1* | 6/2009 | Squires ..................... 424/130.1 |

OTHER PUBLICATIONS

Parman et al Nature Medicine vol. 5 p. 582 (1999).*
Conlon et al, Exogenous retinoic acid rapidly induces anterior ectopic expression of murine Hox-2 genes in vivo, Development, 1992, pp. 357-368, vol. 116.
Grotewold et al, The Wnt antagonist Dickkopf-1 is regulated by Bmp signaling and c-Jun and modulates programmed cell death, EMBO J, 2002, pp. 966-975, vol. 21, No. 5.
Hagen et al, Signalling activity of β-catenin targeted to different subcellular compartments, Biochem. J., 2004, pp. 471-477, vol. 379.

Hansen et al, A novel hypothesis for thalidomide-induced limb teratogenesis: redox misregulation of the NF-kappaB pathway, Antioxid Redox Signal, 2004, pp. 1-14, vol. 6, No. 1.
Kohlhase et al, Mutations at the SALL4 locus on chromosome 20 result in a range of clinically overlapping phenotypes, including Okihiro syndrome, Holt-Oram syndrome, acro-renal-ocular syndrome, and patients previously reported to represent thalidomide embryopathy, J Med Genet, 2003, pp. 473-478, vol. 40.
Korinek et al, Constitutive transcriptional activation by a beta-catenin-Tcf complex in APC-/- colon carcinoma, Science, 1997, pp. 1784-1787, vol. 275, No. 5307.
Lenz, W, A short history of thalidomide embryopathy, Teratology, 1988, pp. 203-215, vol. 38, No. 3.
Maass et al, Atherogenetically relevant cells support continuous growth of *Chlamydia pneumoniae*, Herz, 2000, pp. 68-72, vol. 25, No. 2.
Mellin et al, The saga of thalidomide. Neuropathy to embryopathy, with case reports of congenital anomalies, N. Engl J Med, 1962, pp. 1184-1193, vol. 267, No. 23.
Montero et al, Role of FGFs in the control of programmed cell death during limb development, Development, 2001, pp. 2075-2084, vol. 128.
Mukhopadhyay et al, Dickkopf1 Is Required for Embryonic Head Induction and Limb Morphogenesis in the Mouse, Developmental Cell, 2001. pp. 423-434, vol. 1.
Pizette et al, BMPs negatively regulate structure and function of the limb apical ectodermal ridge, Development, 1999, pp. 883-894, vol. 126.
Qiang et al, Wnt signaling in B-cell Neoplasia, Oncogene, 2003, pp. 1536-1545, vol. 22.
Shaughnessy et al, Interpreting the molecular biology and clinical behavior of multiple myeloma in the context of global gene expression profiling, Immunol Rev, 2003, pp. 140-163, vol. 194.
Smithells et al, Recognition of thalidomide defects, J Med Genet, 1992, pp. 716-723, vol. 29.
Stephens et al, Mechanism of action in thalidomide teratogenesis, Biochem Pharmacol, 2000, pp. 1489-1499, vol. 59, No. 12.
Yokouchi et al, BMP-2/-4 mediate programmed cell death in chicken limb buds, Development, 1996, pp. 3725-3734, vol. 122.
Zimmerman et al, The Spemann Organizer Signal noggin Binds and Inactivates Bone Morphogenetic Protein 4, Cell, 1996, pp. 599-606, vol. 86.
Zuzarte-Luis et al, A new role for BMP5 during limb development acting through the synergic activation of Smad and MAPK pathways, Dev Biol., 2004, pp. 39-52, vol. 272, No. 1.

* cited by examiner

*Primary Examiner*—Sheela J Huff

(57) ABSTRACT

Pharmaceutical compositions comprising anti-teratogenic agents are disclosed. Additionally, pharmaceutical compositions comprising anti-neoplastic agents and anti-teratogenic agents are disclosed. Methods of assessing the teratogenicity of a compound are disclosed. The present invention further comprises applications of the aforementioned compositions and methods.

8 Claims, 7 Drawing Sheets

PHARMACEUTICAL COMPOSITIONS COMPRISING AN ANTI-TERATOGENIC COMPOUND AND APPLICATIONS OF THE SAME

STATEMENT REGARDING FEDERALLY SPONSORED RESEARCH

This work was funded by grant CA55819 and CA97513 from the National Institutes of Health. The government has certain rights in this invention.

BACKGROUND AND BRIEF SUMMARY OF THE INVENTION

Thalidomide was originally used as a sedative to treat morning sickness. However, thalidomide administration during pregnancy resulted in congenital defects in thousands of human fetuses. Many tissues and organs like eyes and heart, for example, are affected by thalidomide during embryonic development. Additionally, variable limb truncations such as amelia (absence of limbs) and phocomelia (proximal limb truncations) are frequent. Thalidomide is now used to treat leprosy and multiple myeloma. Additionally, thalidomide has been used in a treatment of a variety of other conditions including, but not limited to, chronic graft versus host disease, rheumatoid arthritis, sarcoidosis, inflammatory skin diseases and inflammatory bowel disease.

Thalidomide is a racemic chemical compound that may be described chemically as 2-(2,6-dioxo-3-piperidyl)isoindole-1,3-dione or α-(N-phthalimido)glutarimide. The empirical formula for thalidomide is $C_{13}H_{10}N_2O_4$, and the gram molecular weight is 258.2. The CAS number of thalidomide is 50-35-1.

Lenalidomide, a thalidomide analogue, is an immunomodulatory agent with anti-angiogenic properties. The chemical name is 3-(4-amino-1-oxo 1,3-dihydro-2H-isoindol-2-yl)piperidine-2,6-dione. The empirical formula for lenalidomide is $C_{13}H_{13}N_3O_3$, and the gram molecular weight is 259.3.

The teratogenic effect of thalidomide is species-specific. Thalidomide exposure to certain non-human primates in-utero induces limb malformations identical to those seen in humans. Certain standard model organisms like mice and rats are thalidomide-resistant, while New Zealand White rabbits and chickens show thalidomide-induced embryopathies. In humans and rabbits, the result of thalidomide treatment is primarily phocomelia, whereas in chicken limbs both proximal and distal structures are affected. In extreme cases, all three organisms display amelia.

Thalidomide induces oxidative stress through the formation of free radical-initiated reactive oxygen species (ROS) in limb bud cells and embryos of thalidomide-sensitive rabbits but not in those of thalidomide-resistant mice or rats. The cellular response to ROS production primarily consists of removal of free radicals through the reduced glutathione (GSH)-dependent detoxification pathways. GSH is oxidized to glutathione disulfide in the detoxification processes, which leads to a shift in the intracellular redox potential and results in a more oxidative environment. Dramatic oxidative intracellular redox potentials can modulate signaling and gene expression thereby inducing apoptosis. The overall embryonic redox potential and especially that of limb buds is much more oxidative in thalidomide-sensitive rabbits than in thalidomide-resistant rats. Furthermore, rat limb buds possess higher GSH stores to buffer redox potentials altered by ROS than do rabbit limb buds (1).

The soluble Wnt inhibitor Dickkopf1 (Dkk1) and canonical Wnt/β-catenin signaling are involved in limb morphogenesis. Dkk1 is known to promote programmed cell death (PCD) in the developing limb and Dkk1 expression is induced by Bmp4 and Bmp5. All bone morphogenetic proteins (Bmps) with important functions during limb development (Bmp2, -4, -5 and -7) signal through the same Bmp type I receptor (BmpR-IA) in the limb mesenchyme, and Bmp2 and Bmp7 may also regulate Dkk1 expression.

Thalidomide induces limb and eye defects in the chicken embryo at an $EC_{50}$ of 50 μg/kg egg weight and apoptosis in primary human embryonic fibroblasts (HEFs) at an $EC_{50}$ of 8.9 μM. Using these model systems, the present inventors demonstrate by semi-quantitative RT-PCR and whole-mount in situ hybridization that thalidomide-induced oxidative stress enhances signaling through Bmps. This leads to up-regulation of the Bmp target gene and Wnt antagonist Dickkopf1 (Dkk1) with subsequent inhibition of canonical Wnt/β-catenin signaling and increased cell death. Thalidomide-induced cell death is dramatically reduced in HEFs and in embryonic limb buds by the use of inhibitors against Bmps, Dkk1 and Gsk3β, a β-catenin antagonist acting downstream of Dkk1 in the Wnt pathway. Additionally, blocking of Dkk1 or Gsk3β dramatically counteracts thalidomide-induced limb truncations and microphthalmia. Thus, perturbing Bmp/Dkk1/Wnt signaling is central to the teratogenic effects of thalidomide.

In various embodiments, the present invention is a pharmaceutical composition comprising an anti-neoplastic agent and an anti-teratogenic agent. In further embodiments, the present invention is a pharmaceutical composition for blocking the teratogenicity of an anti-neoplastic agent comprising an agent that activates the Wnt signaling pathway downstream of the Wnt ligand-receptor interaction.

In addition to the aforementioned compositions, the present invention embodies a method of inhibiting the teratogenicity of an anti-neoplastic agent comprising administering a pharmaceutical composition comprising an agent that activates the Wnt signaling pathway downstream of the Wnt ligand-receptor interaction.

In a particular embodiment, a method of assessing the teratogenicity of a compound is disclosed. Such a method comprises: administering the compound to a cell and observing whether there is activation of the Wnt signaling pathway downstream of the Wnt ligand-receptor interaction in comparison to an untreated cell.

In yet another embodiment, there is disclosed a method of treating a mammalian subject comprising administering to said mammalian subject an effective amount of a pharmaceutical composition comprising an anti-neoplastic agent and an anti-teratogenic agent.

The included drawings and examples illustrate and exemplify the embodiments of the invention as further described herein.

Limb and eye defects were induced by thalidomide at an $EC_{50}$ of 50 µg/kg egg weight. (B, C) 100-120 embryos were analyzed for each stage and each kind of treatment. (D-F) Skeletal preparations were made from thalidomide-treated (Th+) and solvent-treated (Th−) day 6-7 embryos and stained for cartilage. Developing wings are shown in (D) and (E). Note that in (F) (whole embryo, dorsal view) only the left hindlimb is truncated whereas the right hindlimb and the wings appear to be normal. a, autopod; sc, scapula; st, stylopod; z, zeugopod. (G, H) Heads of day 7 embryos are shown. A mild (G, right) and a severe (H) form of microphthalmia is presented. (I, J) Embryos were treated as indicated and the ratio of embryos showing limb truncations (I) or microphthalmia (J) is given. For one single experiment, between 50 and 60 embryos were analyzed for each kind of treatment. Any diagram represents mean values and standard deviations from four independent experiments. Chi-square test: *, $P<0.001$, related to solvent-treated control embryos. phthal, phthalimide; rac, racemic thalidomide; S-thal, (S)-(−) thalidomide; R-thal, (R)-(+) thalidomide.

Figure 2:
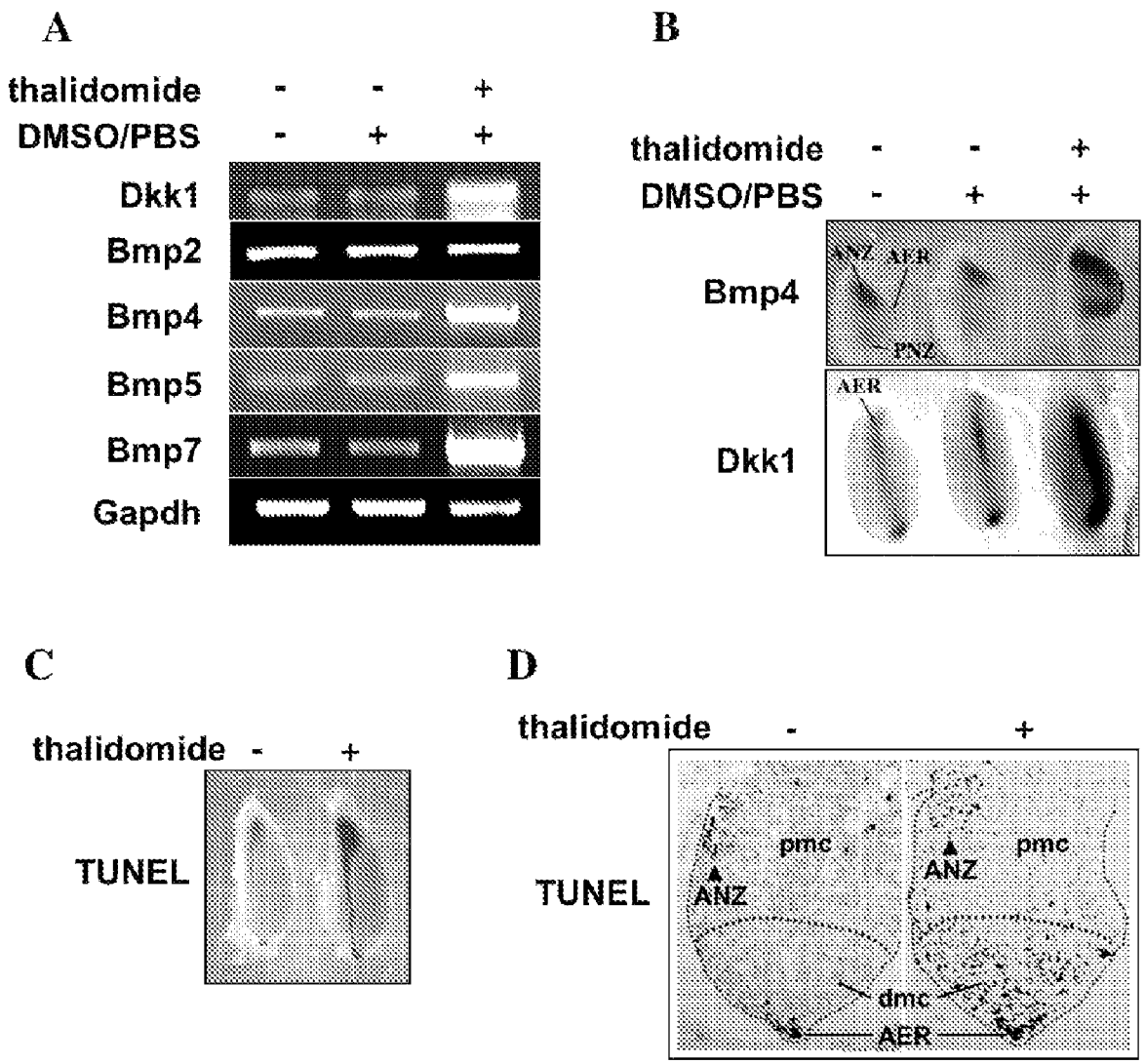

FIG. 2. Thalidomide induces Dkk1 and Bmp expression as well as apoptosis in limb buds. Analyses were performed with HH stages 23/24 chicken embryos that were treated as indicated. (A) sqRT-PCRs were carried out with RNA isolated from pooled wing and hindlimb buds of 60 untreated, solvent treated or thalidomide-treated embryos. GAPDH was used for normalization. One representative set of sqRT-PCRs of three independent experiments is shown. (B) Whole mount in situ hybridizations with Dkk1 and Bmp4 probes and (C) whole mount TUNEL staining were carried out on wing and hindlimb buds. Representative sets of hindlimb buds (Dkk1, distal view; TUNEL, distal view) and wing buds (Bmp4, dorsal view) are shown. Anterior is always on the top. (D) TUNEL staining of wing bud cross sections. The dark spots indicate PCD. Dorsal is on the right. dmc, distal mesenchyme; pmc, proximal mesenchyme.

Figure 3:
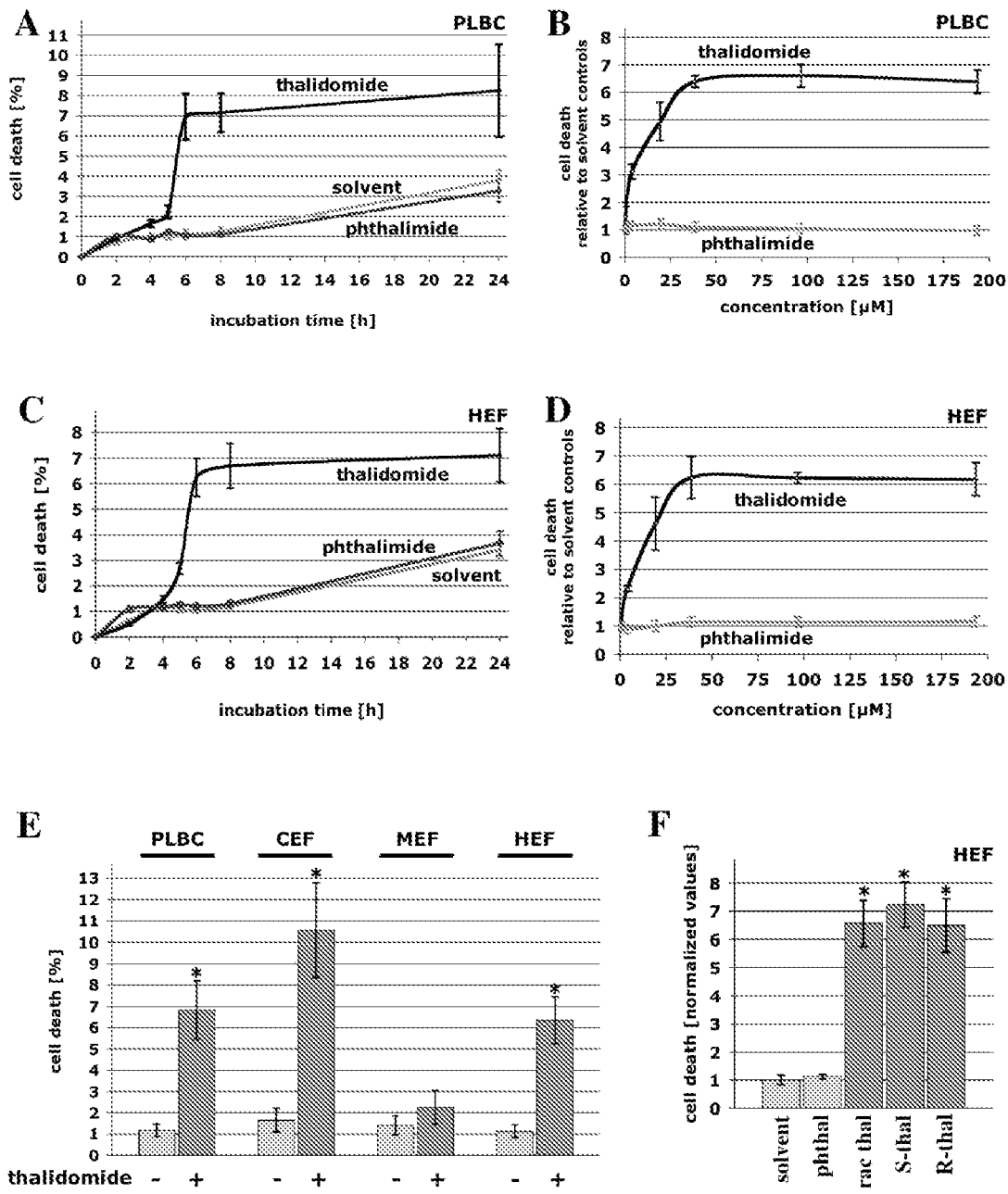

FIG. 3. Thalidomide induces cell death in primary embryonic cells of thalidomide-sensitive species. (A-D) For time course experiments in PLBCs (A) or HEFs (C), thalidomide or phthalimide were applied at 38.7 µM (thalidomide, 10 µg/ml; phthalimide, 5.7 µg/ml). For dose response experiments, PLBCs (B) or HEFs (D) were treated with drugs for six hours. The ratios of dead to live cells were determined after incubation. For the dose-response curves, these numbers were normalized to solvent controls. Each diagram represents four individual experiments. Standard deviations are indicated. PCD was induced by thalidomide at $EC_{50}$ values of 5.0 µM (PLBCs) or 8.9 µM (HEFs). (E) Cells as indicated were treated with thalidomide (+) or solvent (−). Shown are the ratios of dead to live cells. The data represent in each case eight individual experiments. Standard deviations are indicated. Students t-test (two-tailed): *, $P<10^{-5}$, related to solvent controls. (F) HEFs were treated with thalidomide forms as indicated at 10 µg/ml and the ratios of dead to live cells were determined. The data represent in each case four individual experiments. The values were normalized to solvent controls exhibiting the basal level of cell death under the given conditions. Standard deviations are indicated. Students t-test (two-tailed): *, $P<10^{-5}$, relative to solvent controls. phthal, phthalimide; rac, racemic thalidomide; S-thal, (S)-(−) thalidomide; R-thal, (R)-(+) thalidomide.

Figure 4:
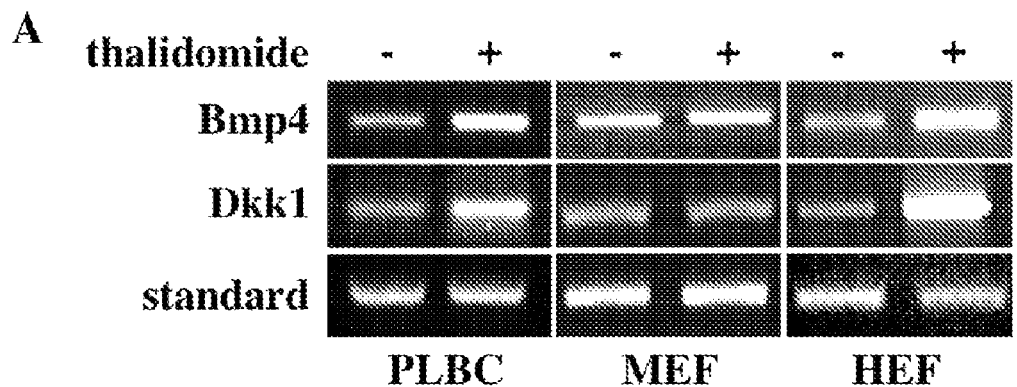
Figure 4:
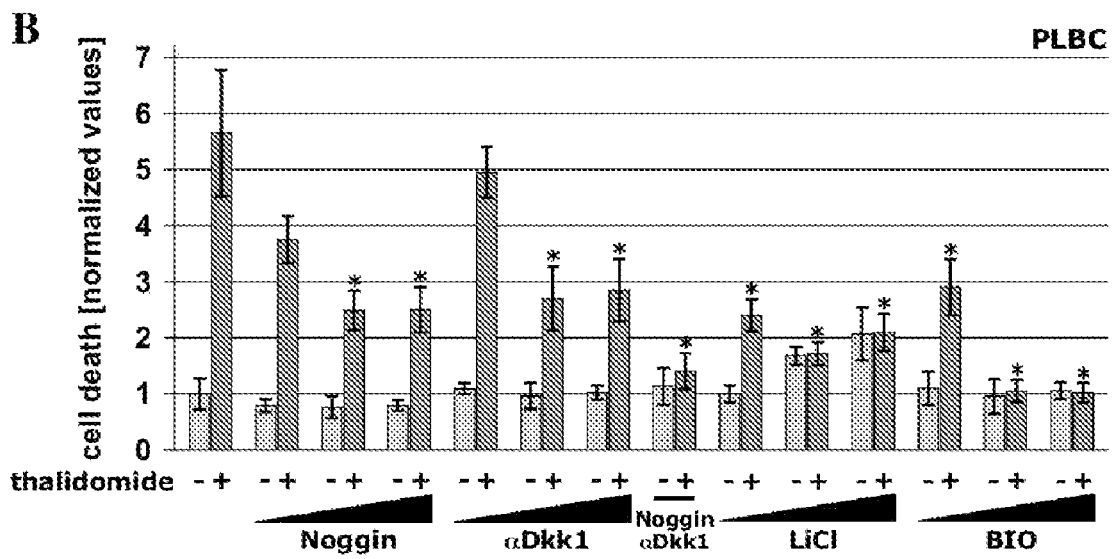
Figure 4:
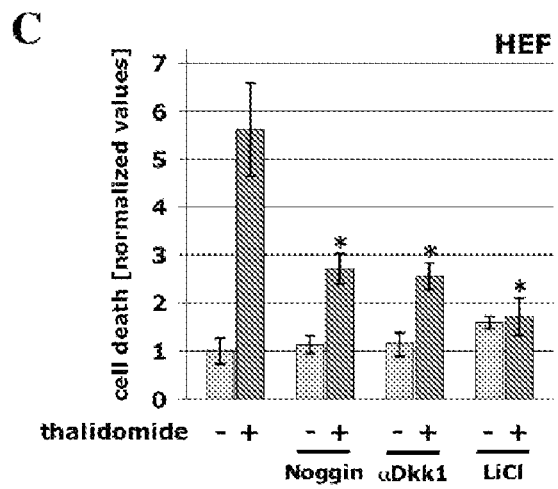

FIG. 4. Blocking of Bmps, Dkk1 or Gsk3β antagonizes thalidomide-induced cell death in embryonic cells of thalidomide-sensitive species. PLBCs, MEFs or HEFs were treated with thalidomide (+) or solvent (−) and reagents as indicated. The relative transcription levels of the given genes (A) or the ratios of dead to live cells (B, C) were determined after incubation. For standardization in (A), GAPDH (PLBCs) or HPRT (MEFs, HEFs) was used. For each cell type, one representative set of sqRT-PCRs of three independent experiments is shown. (B, C) The triangles indicate increasing concentrations. The data represent in each case at least eight individual experiments. The values were normalized to negative controls (cells treated exclusively with solvent). Standard deviations are indicated. Students t-test (two-tailed): *, $P<10^{-5}$, related to thalidomide-treated cells. BIO, Gsk3-Inhibitor IX.

Figure 5:
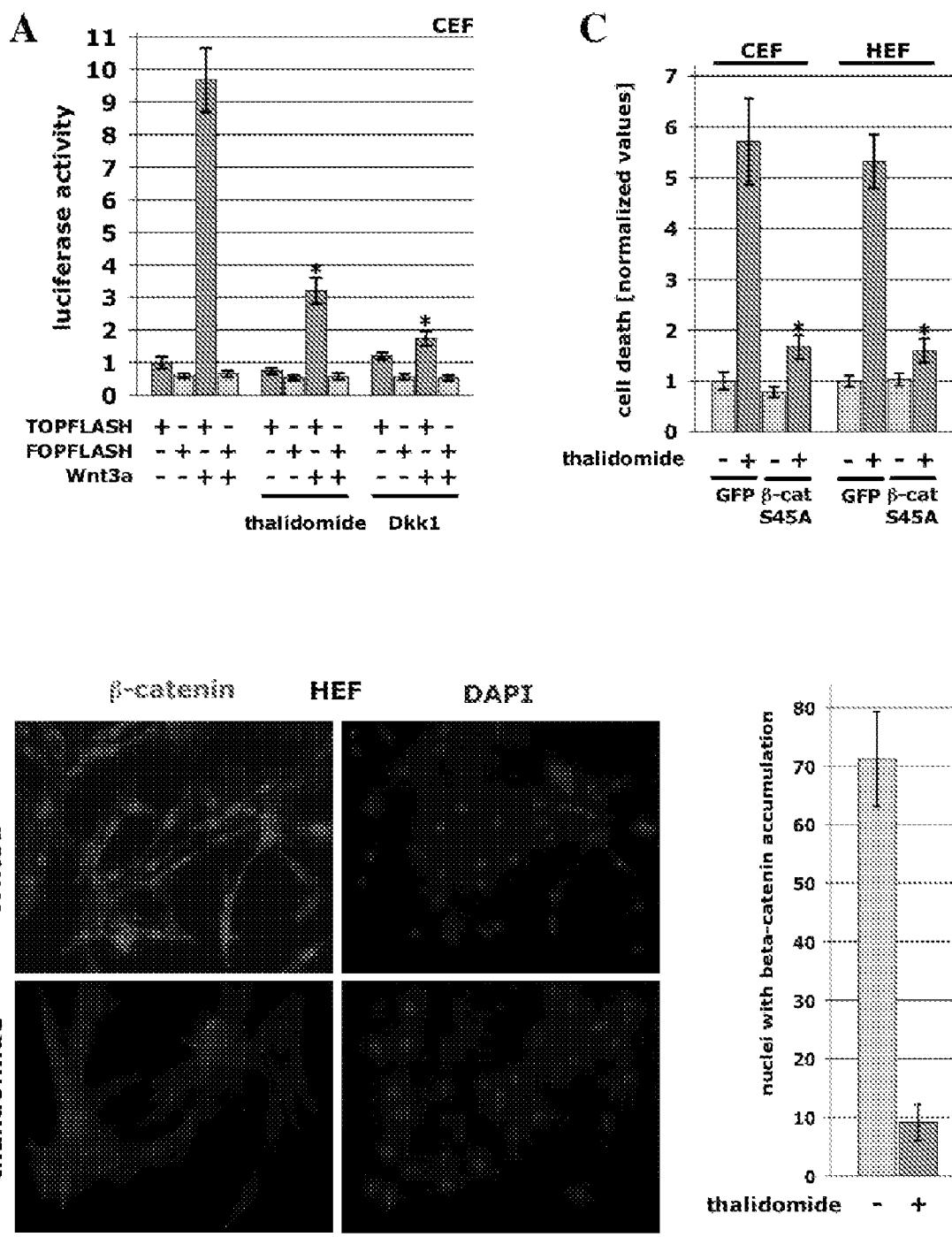

FIG. 5. Thalidomide blocks canonical Wnt signaling. (A) CEFs were transfected with TOPflash or FOPflash (negative control) and incubated with Wnt3a-conditioned-medium or with control medium. Values were normalized to TOPflash-transfected cells that were incubated with control medium and to the number of living cells. n=8, standard deviations are indicated. Students t-test (two-tailed): *, $P<3\times10^{-9}$ related to Wnt3a-treated TOPflash-transfected cells. (B) Sub-cellular localization of β-catenin in Wnt3a- or Wnt3a- and thalidomide-treated HEFs. DAPI was used for nuclear staining (control). The diagram summarizes the proportion of nuclei with a clear fluorescent signal in relation to the total number of nuclei of three independent experiments. (C) CEFs or HEFs were transfected with constructs encoding constitutively active β-catenin (S45A) or GFP and treated with thalidomide (+) or solvent (−). After incubation, the ratios of dead to live cells were determined. Values were normalized to GFP/solvent controls. n=9, standard deviations are indicated. Students t-test (two-tailed): *, $P<10^{-6}$ related to GFP-transfected thalidomide-treated cells.

Figure 6:
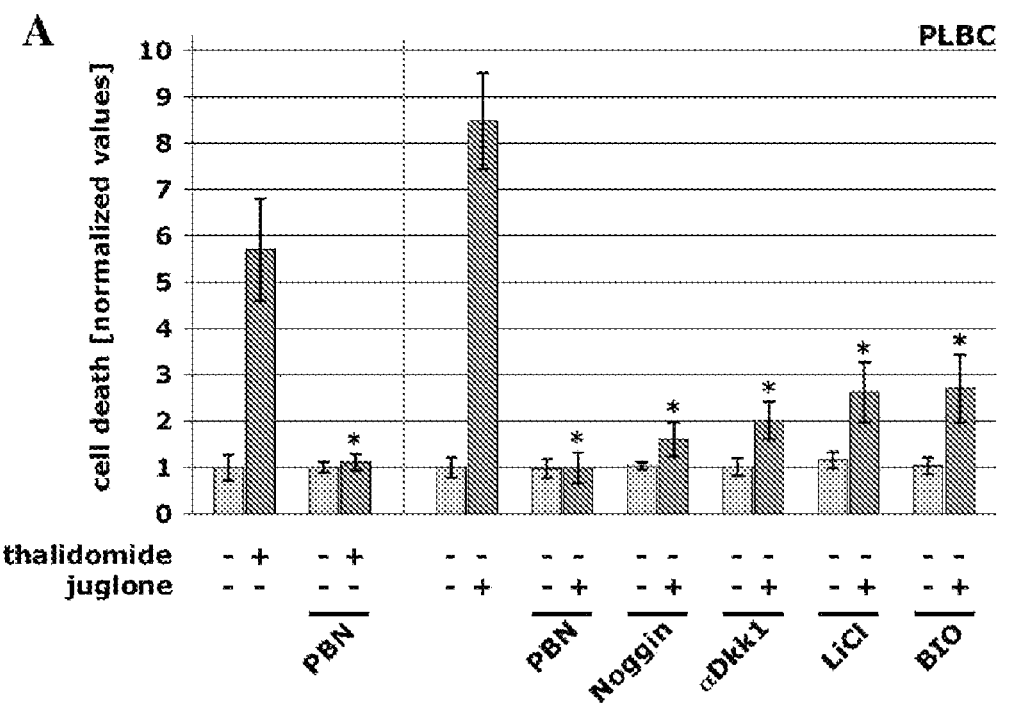
Figure 6:
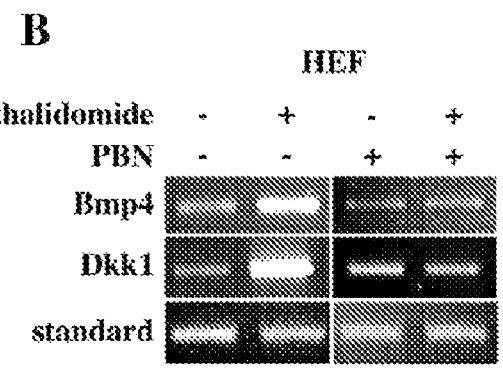
Figure 6:
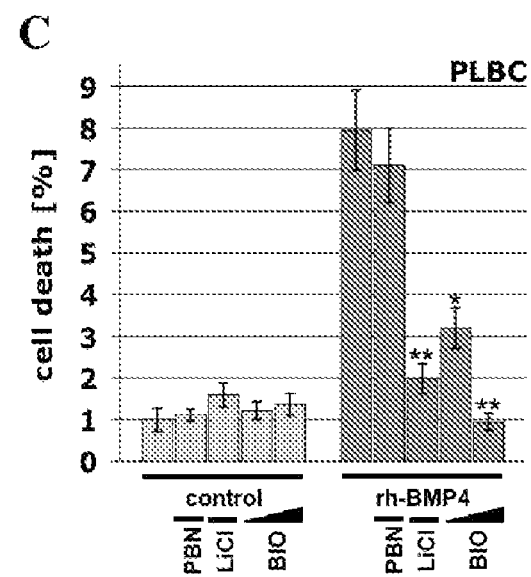

FIG. 6. The up-regulation of Bmp signaling is a consequence of thalidomide-induced oxidative stress. (A) PLBCs were treated as indicated, and after incubation the ratios of dead to live cells were determined. Values were normalized to solvent controls. n=8, standard deviations are indicated. Students t-test (two-tailed): *, $P<10^{-8}$ related to thalidomide- or to juglone-treated cells. (B) HEFs were treated as indicated and relative transcription levels of the given genes were investigated by sqRT-PCR. HPRT was used for standardization. One representative set of sqRT-PCRs of two independent experiments is shown. (C) PLBCs were treated as indicated. The data summarize the ratios of dead to live cells of four individual experiments. Values were normalized to the negative control (untreated cells). Standard deviations are indicated. Students t-test (two-tailed): *, $P<10^{-3}$, **, $P<10^{-5}$, related to Bmp4-treated cells. The triangle indicates increasing concentrations of BIO (Gsk3-Inhibitor IX). It should be noted that pre-treatment with 2 mM PBN completely reduces thalidomide- and juglone-induced cell death (A) whereas it has no significant effect on Bmp4-induced cell death (C).

Figure 7:
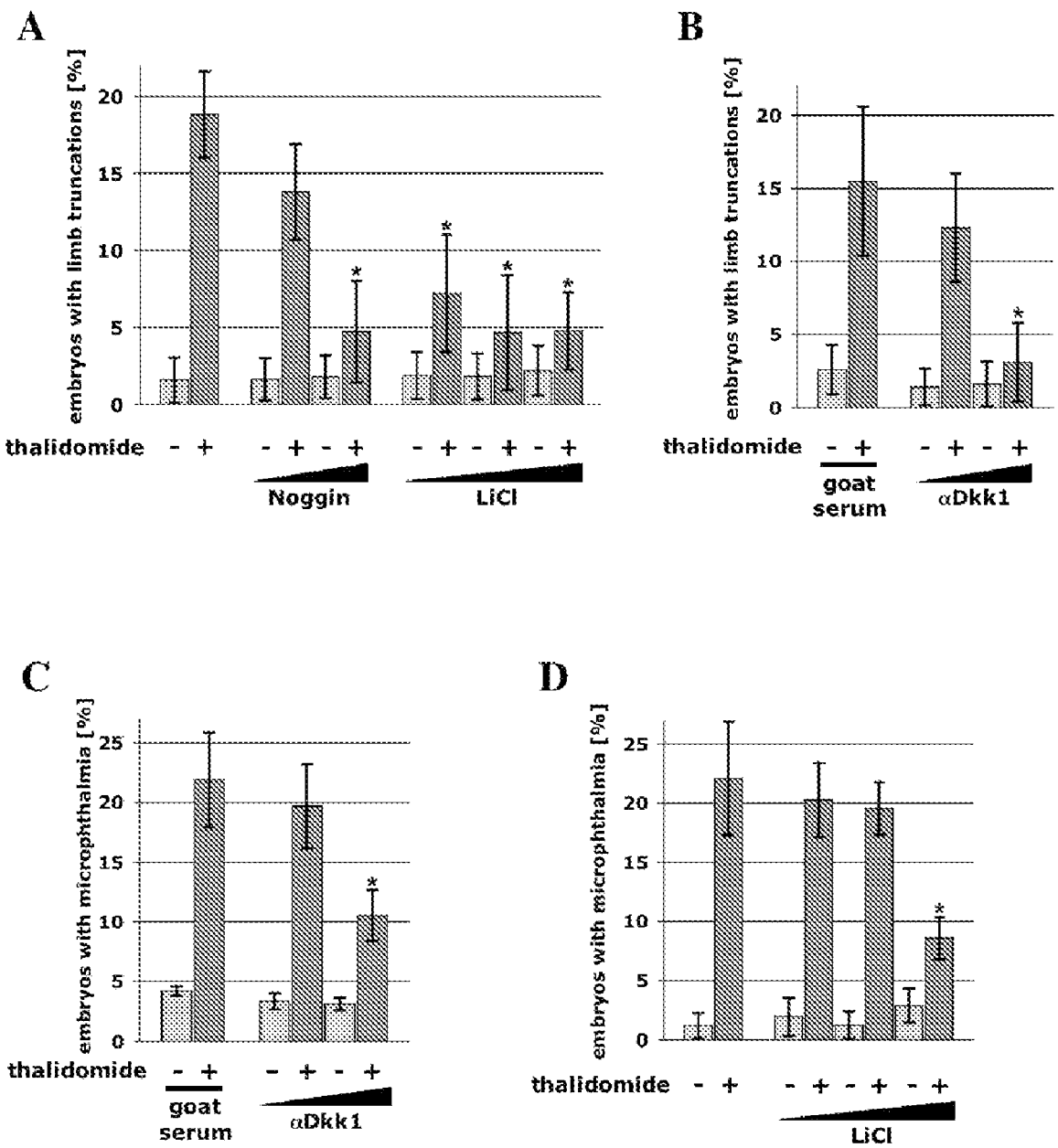

FIG. 7. Noggin, LiCl and Dkk1 antiserum antagonize thalidomide-induced limb truncations and microphthalmia in chicken embryos. Embryos were treated as indicated (goat serum: serum of non-immunized goats; αDkk1: Dkk1 specific goat IgG) and the ratio of embryos showing limb truncations (A, B) or microphthalmia (C, D) is given. The triangles indicate increasing Noggin, αDkk1 antibody or LiCl dosages. For one single experiment between 35 and 45 embryos were analyzed for each kind of treatment. Any diagram represents mean values and standard deviations from four independent experiments. Chi-square test: *, $P<0.01$, related to thalidomide (A, D) or to thalidomide and goat serum (B, C) treated embryos.

DETAILED DESCRIPTION

"Dkk" is meant to refer to the nucleic acids and proteins of members of the Dkk (Dickkopf) family. This includes, but is not limited to, Dkk1, Dkk-2, Dkk-3, Dkk-4, Soggy, and related Dkk proteins. Dkk1 is a preferred embodiment of the present invention. However, the Dkk proteins have substantial homology and one skilled in the art will appreciate that certain embodiments of the present invention utilizing Dkk1 may also be utilized with the other Dkk proteins.

"Dkk1" is meant to refer to the Dkk1 protein and nucleic acids which encode the Dkk1 protein. Dkk1 refers to Dickkopf-1. Dkk1 was first identified in *Xenopus* and recognized as a factor capable of inducing ectopic head formation in the presence of inhibition of the BMP pathway. It was then also found to inhibit the axis-inducing activity of several Xenopus Wnt molecules by acting as an extracellular antagonist of Wnt signaling. Mammalian homologs have been found including Dkk1, Dkk-2, Dkk-3, Dkk-4 and Soggy. Human Dkk1 was also referred to as sk. Dkk1 is meant to include proteins from any species having a Wnt pathway in which Dkk1 interacts including mammalian species (e.g., *murine, caprine, canine, bovine, feline, equine, primate, ovine, porcine* and the like), with particularly preferred mammals being humans. Nucleic acid sequences encoding Dkk1 include, but are not limited to human Dkk1 (GenBank Accession Nos. AH009834, AF261158, AF261157, AF177394, and AF127563). The genomic sequences with exon annotation are GenBank Accession Nos. AF261157 and AF261158. Also contemplated are homologs of these sequences which have Dkk1 activity in the Wnt pathway. Dkk1 amino acid sequences include, but are not limited to human dickkopf homolog 1 (GenBank Accession Nos. AAG15544, BAA34651, MF02674, and AAD21087). Variants and homologs of these sequences which possess Dkk1 activity are also included when referring to Dkk1.

"GSK3" refers to the enzyme glycogen synthase kinase-3. Two similar isoforms of the enzyme, termed GSK3α and GSK3β, have been identified. GSK3, unlike other protein kinases that are typically activated by signaling pathways, is normally activated in resting cells, and its activity is attenuated by the activation of certain signaling pathways such as after the binding of insulin to its cell-surface receptor. Activation of the insulin receptor leads to the activation of protein kinase B (PKB, also called Akt), which in turn phosphorylates GSK3, thereby inactivating it. The inhibition of GSK3 leads to the activation of glycogen synthesis. GSK3 is meant to include proteins from any species having including mammalian species (e.g., *murine, caprine, canine, bovine, feline, equine, primate, ovine, porcine* and the like), with particularly preferred mammals being humans. Nucleic acid sequences encoding GSK3 include, but are not limited to human GSK3β (GenBank Accession Nos. L33801). Variants and homologs of these sequences which possess GSK3 activity are also included when referring to GSK3.

"Noggin" refers to the 232-amino acid secreted protein as typified by GenBank Accession No. NM_005450 and the nucleic acids encoding the protein. The Noggin protein is known to bind numerous growth factors such as Bmp4. Also contemplated are homologs of these sequences and mutants that retain similar functional characteristics to native Noggin.

"Gene" refers to a DNA sequence that encodes through its template or messenger RNA a sequence of amino acids characteristic of a specific peptide. The term "gene" includes intervening, non-coding regions, as well as regulatory regions, and can include 5' and 3' ends.

"Nucleic acid" is meant to include single stranded and double stranded nucleic acids including, but not limited to DNAs, RNAs (e.g., mRNA, tRNAs, siRNAs), cDNAs, recombinant DNA (rDNA), rRNAs, antisense nucleic acids, oligonucleotides, and oligomers, and polynucleotides. The term may also include hybrids such as triple stranded regions of RNA and/or DNA or double stranded RNA:DNA hybrids. The term also is contemplated to include modified nucleic acids such as, but not limited to biotinylated nucleic acids, tritylated nucleic acids, fluorophor labeled nucleic acids, inosine, and the like.

"Gene sequence" refers to a nucleic acid molecule, including a non-transcribed or non-translated DNA sequence, which comprises a gene. The term is also intended to include any combination of gene(s), gene fragment(s), non-transcribed sequence(s) or non-translated sequence(s) which are present on the same DNA molecule.

"Expression" refers to the process comprising transcription of a gene sequence and subsequent processing steps, such as translation of a resultant mRNA to produce the final end product of a gene. The end product may be a protein or a nucleic acid.

"EC50" refers to the molar concentration of an agonist, which produces 50% of the maximum possible response for that agonist.

Thalidomide induces limb and eye defects in the chicken embryo at an $EC_{50}$ of 50 µg/kg egg weight and apoptosis in primary human embryonic fibroblasts (HEFs) at an $EC_{50}$ of 8.9 µM. Using these model systems, the present inventors demonstrate by semi-quantitative RT-PCR and whole-mount in situ hybridization that thalidomide-induced oxidative stress enhances signaling through Bmps. This leads to up-regulation of the Bmp target gene and Wnt antagonist Dickkopf1 (Dkk1) with subsequent inhibition of canonical Wnt/β-catenin signaling and increased cell death. Thalidomide-induced cell death is dramatically reduced in HEFs and in embryonic limb buds by the use of inhibitors against Bmps, Dkk1 and Gsk3β, a β-catenin antagonist acting downstream of Dkk1 in the Wnt pathway. Additionally, blocking of Dkk1 or Gsk3β dramatically counteracts thalidomide-induced limb truncations and microphthalmia. Thus, perturbing Bmp/Dkk1/Wnt signaling is central to the teratogenic effects of thalidomide.

The present inventors demonstrate that thalidomide-induced limb defects and microphthalmia (small eyes) are caused by an oxidative stress mediated up-regulation of Bmp signaling. As a consequence, Dkk1 expression is induced leading to an inhibition of canonical Wnt signaling and increased programmed cell death (PCD). Both thalidomide-induced PCD and birth defects can be inhibited by blocking Dkk1 or by activating canonical Wnt signaling downstream of the ligand-receptor interaction. Furthermore, thalidomide induces identical molecular changes in both the chicken model system and primary human embryonic cells.

Thalidomide-induced PCD, limb truncations and microphthalmia result through a cascade of events that includes ROS generation, enhanced Bmp signaling, activation of the Wnt antagonist Dkk1 and suppression of canonical Wnt/β-catenin signaling. Thalidomide-induced embryopathy may be traced to increased levels of ROS.

Bmps promote PCD during normal embryonic limb and eye development. Furthermore, Bmp4 and Dkk1 are co-expressed at the sites of PCD in limb buds, Dkk1 is a Bmp4 target gene, and Dkk1 induces PCD during embryonic limb development. Neutralizing ROS and activating β-catenin by inhibiting Gsk3β completely counteracts thalidomide-induced PCD. Bmp4-induced cell death is completely counteracted by Gsk3β inhibitors but remains unaffected when ROS is neutralized. Furthermore, counteracting ROS abolishes thalidomide-induced up-regulation of Bmp4 and Dkk1 expression. Thus, the present inventors demonstrate that thalidomide initially induces ROS formation that in turn causes enhanced Bmp signaling. This leads to the hyperexpression of the Wnt antagonist Dkk1 and subsequent suppression of Wnt signaling. The diminished β-catenin activity ultimately leads to increased PCD that is responsible for the limb and eye defects during embryonic development.

Thalidomide-induced molecular pathologies involve a spectrum of events. For example, individual use of either Noggin or anti-Dkk1 antibody alone causes only a partial neutralization of thalidomide-induced PCD in cell culture whereas the combined use of these agents results in complete inhibition. Moreover, enhanced Bmp expression and PCD were observed in 55% of the limb buds whereas Dkk1 expression was only increased in 30%. Thus, thalidomide-induced Bmp signaling may cause PCD independent of Dkk1.

Gsk3β inhibition completely blocks thalidomide-induced PCD in cell culture and dramatically reduces the number of embryos showing limb and eye malformations. Beside its crucial role in canonical Wnt signaling, Gsk3β is a direct downstream target of the protein kinase Akt (protein kinase B). Akt activity is stimulated through Wnt signaling and activated Akt blocks Gsk3β thereby preventing β-catenin degradation (45).

In chicken embryos, thalidomide causes severe distal limb truncations but also affects proximal structures. For example, thalidomide affects stylo-, zeugo- and autopods. Drug-induced PCD occurs in the distal tip of the chicken limb bud including the AER. Enhanced PCD within the AER mimics AER depletion, and it has been reported that AER depletion disturbs proximo-distal outgrowth resulting in severe distal limb truncations (47, 48). In the chicken limb bud, thalidomide also enhances PCD in the ANZ, which is responsible for patterning. ANZ enlargement is likely not reflected by a prevalence of anterior defects in the resulting anatomy because AER disruption is dominant.

The present data demonstrate that thalidomide induces apoptosis in distal mesenchymal cells of the limb bud as well as in the AER. Consequently, proximo-distal outgrowth is disturbed resulting in truncated limbs lacking both proximal and distal structures. However, phocomelia is frequent in human thalidomide embryopathy suggesting that in human embryos drug-induced PCD occurs in the distal mesenchymal cells and rarely in the AER. This discrepancy between chicken and human could be explained by differences in the expression pattern of Dkk1, particularly Dkk1 expressed in the AER. However, it will be a challenge for future studies to elucidate these differences between chicken and human thalidomide embryopathy.

Thalidomide induces Bmp signaling and the subsequent expression of Dkk1. The resulting down-regulation of Wnt/β-catenin signaling is important for the teratogenic properties of the drug. Identical molecular consequences were observed in human embryonic fibroblasts (HEFs) demonstrating that the insights gained from studies in the chicken model system are relevant to humans. Importantly, the effect of thalidomide on Bmp/Dkk1/Wnt-signaling is not only restricted to limb bud cells and limb development but has also been shown for fibroblasts isolated from whole embryos and for eye development.

In various embodiments, the present invention is a pharmaceutical composition comprising an anti-neoplastic agent and an anti-teratogenic agent. An anti-neoplastic agent of the present invention includes any anti-neoplastic agent, including but not limited to chemical compounds, proteins, peptides, nucleic acids and the like. In particular embodiments, the anti-neoplastic agent may be selected from the group consisting of thalidomide and lenalidomide.

In a particular configuration of the present embodiment, the anti-teratogenic agent comprises an agent that activates the Wnt signaling pathway downstream of the Wnt ligand-receptor interaction. An agent that activates the Wnt signaling pathway downstream of the Wnt ligand-receptor interaction may be selected from the group consisting of an inhibitor of BMP signaling, an inhibitor of Dkk1, an inhibitor of GSK3-B, and an oxidative stress antagonist. An exemplary inhibitor of BMP signaling comprises Noggin. An exemplary inhibitor of Dkk1 comprises an anti-Dkk1 antibody. Exemplary inhibitors of GSK3-B may be LiCl or GSK3-Inhibitor IX. An exemplary oxidative stress antagonist of the present embodiment is PBN.

Inhibitors of the present invention may also include intracellular inhibitors such as nucleotide based inhibitors that are expressed within a target cell. For example, an anti-sense RNA molecule that inhibits the transcription of Dkk1 would be within the scope of the present invention. General methods for producing anti-sense RNA or other inhibitory nucleotide based molecules in a target cell are within the capabilities of a person having ordinary skill in the relevant art.

In another embodiment, the present invention is a pharmaceutical composition for blocking the teratogenicity of an anti-neoplastic agent. In particular, such a pharmaceutical composition may comprise an agent that activates the Wnt signaling pathway downstream of the Wnt ligand-receptor interaction. In a particular configuration, an agent that activates the Wnt signaling pathway downstream of the Wnt ligand-receptor interaction may be selected from the group consisting of an inhibitor of BMP signaling, an inhibitor of Dkk1, an inhibitor of GSK3-B, and an oxidative stress antagonist. An exemplary inhibitor of BMP signaling comprises Noggin. An exemplary inhibitor of Dkk1 comprises an anti-Dkk1 antibody. Exemplary inhibitors of GSK3-B may be LiCl or GSK3-Inhibitor IX. An exemplary oxidative stress antagonist of the present embodiment is PBN.

In addition to the aforementioned compositions, the present invention embodies a method of inhibiting the teratogenicity of an anti-neoplastic agent comprising administering to a subject in need thereof a pharmaceutical composition comprising an agent that activates the Wnt signaling pathway downstream of the Wnt ligand-receptor interaction. Said agent that activates the Wnt signaling pathway downstream of the Wnt ligand-receptor interaction may be selected from the group consisting of an inhibitor of BMP signaling, an inhibitor of Dkk1, an inhibitor of GSK3-B, and an oxidative stress antagonist. An exemplary inhibitor of BMP signaling comprises Noggin. An exemplary inhibitor of Dkk1 comprises an anti-Dkk1 antibody. Exemplary inhibitors of GSK3-B may be LiCl or GSK3-Inhibitor IX. An exemplary oxidative stress antagonist of the present embodiment is PBN.

In yet another embodiment, there is disclosed a method of treating a mammalian subject comprising administering to said mammalian subject an effective amount of a pharmaceutical composition comprising an anti-neoplastic agent and an anti-teratogenic agent. In particular embodiments, said anti-neoplastic agent is selected from the group consisting of thalidomide and lenalidomide. In more particular embodiments, said anti-teratogenic agent comprises an agent that activates the Wnt signaling pathway downstream of the Wnt ligand-receptor interaction. An agent that activates the Wnt signaling pathway downstream of the Wnt ligand-receptor interaction may be selected from the group consisting of an inhibitor of BMP signaling, an inhibitor of Dkk1, an inhibitor of GSK3-B, and an oxidative stress antagonist. An exemplary inhibitor of BMP signaling comprises Noggin. An exemplary inhibitor of Dkk1 comprises an anti-Dkk1 antibody. Exemplary inhibitors of GSK3-B may be LiCl or GSK3-Inhibitor IX. An exemplary oxidative stress antagonist of the present embodiment is PBN.

In a particular embodiment, a method of assessing the teratogenicity of a compound is disclosed. Such a method comprises administering the compound to a cell and observing whether there is activation of the Wnt signaling pathway downstream of the Wnt ligand-receptor interaction in comparison to an untreated cell.

In various aspects of the aforementioned embodiments, it is anticipated that pharmaceutical compositions will be administered to subjects. Said subjects may be mammalian cells or mammals. In particular, said subjects may be human cells or humans.

EXAMPLES

The following examples are further illustrative of the present invention, but it is understood that the invention is not limited thereto.

Fertilized eggs were purchased from Deindl GmbH, Rietberg-Varensell. They were incubated at 38° C. in a humidified incubator, windowed after one day and staged according to Hamburger and Hamilton (HH stage). Racemic thalidomide (Celgene), thalidomide enantiomers or phthalimide (Sigma) were dissolved in DMSO at 5 mg/ml and further diluted in PBS. Embryos were exposed to drugs by dropping 15 µg-3 mg thalidomide or phthalimide per kg egg weight (about 1-200 µg per embryo) in 50 µl DMSO/PBS as a single dose at HH stages 0-13 onto the embryo. Thalidomide (50 µg) or phthalimide (50 µg) in 10 µl DMSO was injected into the extra-embryonic blood vessels of HH 19 stage embryos. LiCl (99% pure, Sigma) was dissolved in sterile PBS. LiCl (0.1, 0.6 or 3.2 mg) was applied at HH stages 17-19 by dropping 500 µl of a 5 mM, 28 mM or 151 mM LiCl solution onto the embryo. Recombinant Noggin, Dkk1 specific goat IgG (R&D Systems) or serum of non-immunized goats (Sigma) was dissolved in 0.1% BSA/0.01% Fast Green/PBS. Noggin (10 or 100 ng), Dkk1 specific goat IgG (5 or 50 ng) or serum of non-immunized goats (50 ng) was applied to a single embryo at HH stages 17-19 by injecting a 10 µl solution through the extra-embryonic membranes.

Primary limb bud cells (PLBCs) were isolated from 60 pooled wing and hindlimb buds of HH stages 23/24 embryos. Fibroblasts were gained from HH stage 34 chicken embryos or from 13.5 d.p.c. mouse embryos. Human embryonic fibroblasts were provided by Matthias Maass (2). Before adding reagents, all cell types were cultured for 16 hours in D-MEM (Gibco) plus 10% fetal calf serum (FCS) and 2% chicken serum. Treatment with thalidomide, phthalimide, recombinant human (rh) BMP4 (300 ng/ml; R&D Systems), juglone (5 µM; Sigma), recombinant mouse Noggin (30, 300, 1000 ng/ml in FIG. 4B; 300 ng/ml in FIGS. 4C and 6A), anti-human-DKK1 antibody (35, 350 and 1000 ng/ml in FIG. 4B; 350 ng/ml in FIGS. 4C and 6A), LiCl (3, 30, 60 mM in FIG. 4B; 30 mM in FIGS. 4C, 6A and 6C) and/or (2Z,3E)-6-Bromoindirubin-3-oxime (BIO, Gsk3-Inhibitor IX; 50, 500, 1000 nM in FIG. 4B; 500 nM in FIG. 6A; 50 and 500 nM in FIG. 6C; Calbiochem) were performed in Optimem1 (Invitrogen) plus 1% FCS. Unless otherwise noted, all treatments with thalidomide and rh-BMP4 and associated controls were done for six hours. Inhibitors were applied once at the beginning of incubation with the exception of LiCl that was added 150 minutes before harvesting the cells for further analyses. Pre-treatment with phenyl-N-t-butylnitrone (PBN; 2 mM; Sigma) was performed for one hour. Incubations with juglone were performed for two hours, if applicable, after a pre-treatment with PBN, Noggin, anti-Dkk1 antibody, LiCl or Gsk3-Inhibitor IX for one hour.

The morphology of the limbs was studied in specimens fixed in 5% trichloroacetic acid and stained for cartilage with alcian green as described (3).

The β-catenin S45A plasmid encodes a stable and constitutively active form of human β-catenin under the control of a CMV promoter (4). A construct encoding the green fluorescent protein (GFP) downstream of a CMV promoter was used as a control. After transfection with Lipofectamine (Invitrogen) for 24 hours, thalidomide-treatment and measuring of dead cells was performed as further described herein.

Plasmids with wild type (TOPflash) or mutated (FOPflash) LEF/TCF binding sites (5) upstream of a luciferase reporter gene were transiently transfected into CEFs using Lipofectamine (Invitrogen). Following transfection for 24 hours, the cells were exposed to Wnt3a-conditioned medium or to control medium (6) with or without thalidomide or recombinant human DKK1 (150 ng/ml, R&D Biosystems) for 24 hours prior to luciferase assay. Values were normalized for transfection efficiency by co-transfection with a pSV-β-galactosidase vector and for the number of living cells. Luciferase activity was measured using the Dual-Light System (Applied Biosystems).

CEFs or HEFs attached on cover slips were incubated with Wnt3a-conditioned medium including thalidomide or solvent or with control medium for five hours. β-catenin was detected by using a mouse anti-β-catenin antibody (1:500, BD Transduction Laboratories), an anti-mouse Cy3-coupled secondary antibody (Dianova) and fluorescence microscopy. Afterwards, a DAPI staining was performed as a control. Quantification was done by counting the nuclei with a clear fluorescent signal in relation to the number of DAPI-stained nuclei.

RNA isolation, semi-quantitative RT-PCRs and whole mount in situ hybridizations were performed according to standard protocols that are well known within the art. RNA was isolated using TRIZOL (Gibco BRL) followed by DNAseI digestion. First strand synthesis was carried out with the Expand RT System (Roche) according to the manufacturer's instructions. PCR amplification was carried out primers and conditions within the knowledge of a person having skill in the relevant art. Quantifications were performed using NIH Image 1.62.

TUNEL staining was performed as described (7).

Cell death in PLBCs, CEFs, MEFs and HEFs was detected by staining with trypan blue (0.1% (w/v) in PBS; Sigma) for 90 seconds. Cells were counted in a counting chamber to determine the ratio of dead to live cells.

Two-tailed students t-tests and chi-square tests were utilized for statistical analyses.

Example 1

Thalidomide induces limb truncations and microphthalmia in chicken embryos.

Figure 1:
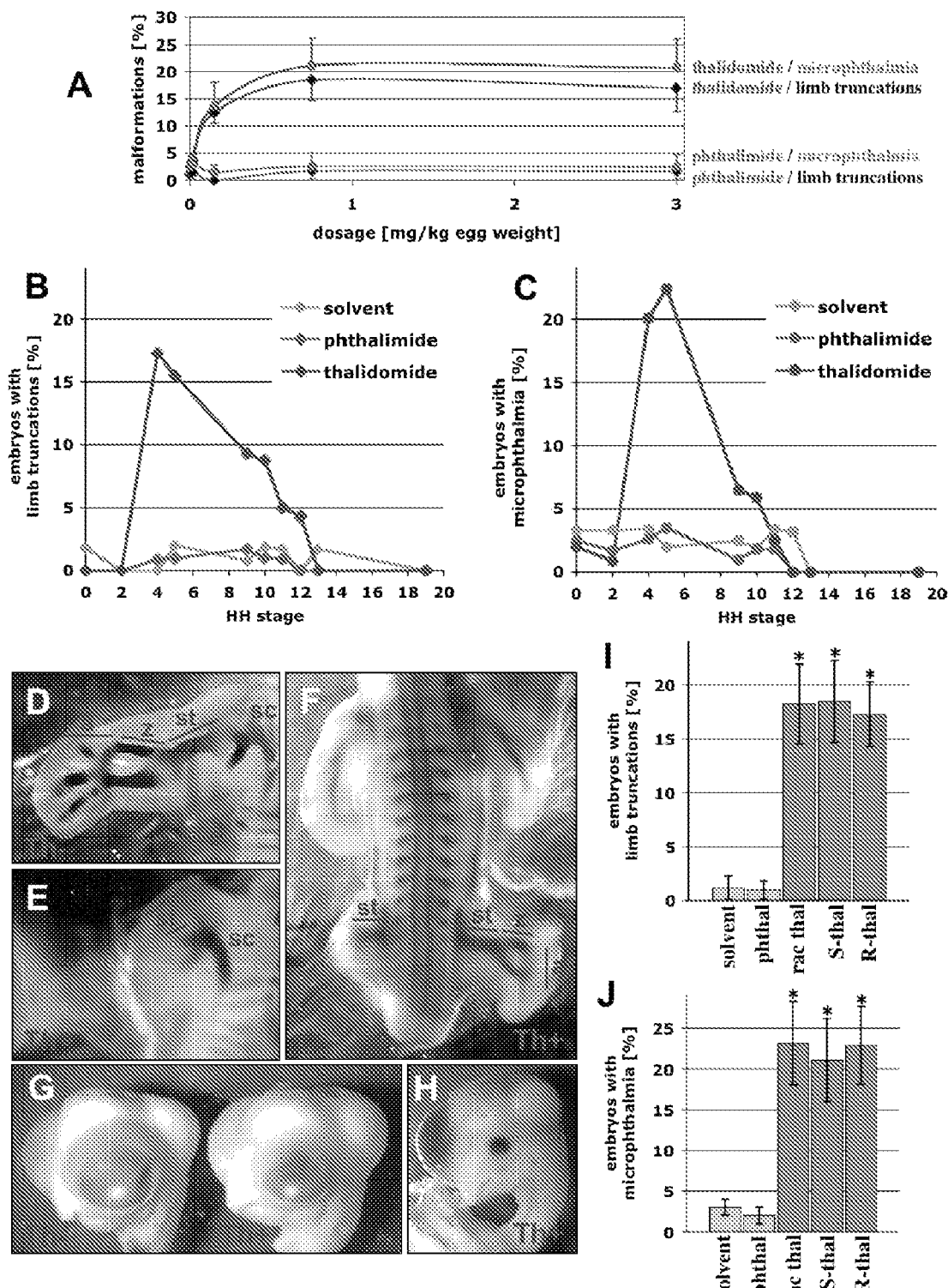
FIG. 1. Thalidomide but not phthalimide induces limb truncations and microphthalmia in chicken embryos. (A-C) Thalidomide or phthalimide was applied at HH stages 4/5 for dose-response (A) or at 0.75 mg/kg egg weight (about 50 μg per embryo) for time course experiments (B, C). The ratios of embryos with limb truncations or microphthalmia are indicated. (A) 50-60 embryos were analyzed for each drug dosage in one experiment. The diagram represents mean values and standard deviations from three independent experiments.

By performing dose-response and time-course experiments the present inventors demonstrated that racemic thalidomide induces a maximum of limb truncations and microphthalmia in chicken embryos when applied at 750 µg/kg egg weight shortly after the primitive streak had fully formed at Hamburger-Hamilton (HH) stages 4/5 (FIG. 1A-C). Therefore, these parameters were used to analyze thalidomide effects on chicken embryonic limb and eye development in detail. Thalidomide-exposed as well as solvent-treated control embryos were analyzed when the three major limb segments, the stylopod, zeugopod and autopod could be demarcated. As a further control, untreated embryos in windowed eggs were also analyzed. About 10% of the embryos of each group died during the first seven days of incubation due to the breeding conditions. Importantly, in comparison to solvent controls, thalidomide did not significantly increase embryonic lethality. Thalidomide-treated embryos that survived until day seven revealed uni- or bilateral limb truncations including amelia (47 of a total of 309 (15%)) (FIG. 1D-F). Besides Amelia, limbs were observed most frequently with a complete lack of zeugopodal and autopodal elements and a dramatically shortened stylopod. In some instances, more mildly affected limbs with missing autopods, truncated zeugopods and complete or nearly complete stylopods were observed.

Both proximal and distal structures were affected in all cases (Table I). Thalidomide caused uni- or bilateral microphthalmia in 21% of the embryos (FIG. 1G, H; Table II). Only about 5% of the embryos showed both limb abnormalities and microphthalmia suggesting that these defects develop independently. In most cases, a severe form of microphthalmia was observed (FIG. 1H). Milder forms were also detected (FIG. 1G). Untreated or solvent-treated control embryos showed little or no evidence of limb malformations (untreated, 0 of 102; solvent-treated, 4 of 212, 2%) or microphthalmia (untreated, 0 of 102; solvent-treated, 6 of 212, 3%). Increasing the amount of thalidomide up to 3 mg/kg egg weight neither influenced the quality nor the quantity of limb truncations or microphthalmia (FIG. 1A; data not shown). The application of thalidomide at later stages clearly reduced the frequency of limb truncations and microphthalmia (FIG. 1B, C). Moreover, in relation to the total number of limb defects, the numbers of amelia and of severe truncations were reduced relative to the milder forms described above (data not shown). Accordingly, the proportion of milder eye defects was increased (data not shown). Consistent with effects of thalidomide exposure being specific to a developmental window, embryonic malformations were not detectable in response to thalidomide applied before HH stage 4 or beyond HH stage 12 (FIG. 1B, C). As a control reagent, the thalidomide-derivative phthalimide was used. Thalidomide is composed of a glutarimide and a phthalimide ring. As expected, phthalimide did not cause limb or eye defects when applied to chicken embryos (FIG. 1A-C, I, J).

In order to investigate the teratogenic effects of the two optical isomers, 750 µg/kg egg weight of (S)-(−)-, (R)-(+)- or racemic thalidomide was applied to chicken embryos at HH stages 4/5. The racemic mixture, the (S)-(−)-enantiomer and the (R)-(+)-enantiomer induced limb deformities in about 18% and eye defects in about 22% of the embryos (FIG. 1I, J). Thus, racemic thalidomide at 750 µg/kg egg weight was used for the following experiments.

Example 2

Thalidomide induces Dkk1 and Bmp expression and apoptosis in limb buds.

Semi-quantitative RT-PCR (sqRT-PCR) analyses using RNA of limb buds of HH stages 23/24 chicken embryos were employed to determine if thalidomide induces Dkk1 expression during early embryonic limb development. In comparison to controls, Dkk1 expression was dramatically enhanced in limb buds of thalidomide-treated embryos (FIG. 2A). Dkk1 expression is governed by Bmp signaling during early limb development (8, 9). The expression of Bmp4, Bmp5 and Bmp7 was clearly up-regulated by thalidomide (FIG. 2A). However, the expression level of Bmp2, another Bmp family member with important functions in limb development, was not significantly affected (FIG. 2A). Bmp and Dkk1 expression were not altered in response to treatment with phthalimide (data not shown).

In limb buds, Bmp4 and Dkk1 are co-expressed in the apical ectodermal ridge (AER) including the underlying mesenchyme and in the anterior and posterior necrotic zones (ANZ, PNZ) (8, 10). Whole mount in situ hybridizations demonstrates that thalidomide induces the transcription of these genes exclusively in their normal expression domains. In 20 of 36 limb buds from thalidomide-treated HH stages 23/24 embryos, Bmp4 expression was dramatically up-regulated in all three domains compared to the controls (FIG. 2B). Furthermore, in 19 of 64 limb buds, Dkk1 expression was also clearly enhanced in the AER and in the underlying mesenchyme as well as in the ANZ. However, expression in the PNZ appeared almost normal (FIG. 2B, data not shown).

Both Bmp4 and Dkk1 are linked to PCD in the developing limb (8, 10, 11). The pattern of apoptosis in limb buds of thalidomide-treated HH stages 23/24 embryos was analyzed. By performing whole mount TUNEL staining, the ANZ, but not the PNZ, is shown to be enlarged in 22 of 40 limb buds. Furthermore, the number of TUNEL-positive cells within the AER was also increased in these limb buds compared to controls (FIG. 2C). In agreement with the distribution of limb anomalies, enhanced PCD was most frequently observed unilaterally in wing buds and bilaterally in hindlimb buds. TUNEL staining on wing bud cross sections demonstrates that thalidomide enhances PCD in the distal mesenchyme, which includes the progress zone (PZ) underlying the AER (FIG. 2D).

Example 3

Blocking of Bmps, Dkk1 or Gsk3β counteracts thalidomide-induced cell death.

The sensitivity of embryonic cells from multiple species to thalidomide-induced cell death in-vitro was studied. First, primary embryonic cells isolated from the mesenchyme of chicken limb buds (primary limb bud cells, PLBCs) were tested for thalidomide sensitivity. Time-course and dose-response experiments revealed that racemic thalidomide caused a maximum of cell death (about 6-fold above control) in PLBCs after six to eight hours of treatment at a concentration of 38.7 µM (10 µg/ml) (FIG. 3A, B, E). Using these parameters, thalidomide also induced PCD six-fold in primary chicken embryonic fibroblasts (CEFs) compared to controls (FIG. 3E). However, the drug did not induce cell death in primary embryonic fibroblasts of mice (MEFs), a species resistant to thalidomide teratogenicity (FIG. 3E). Notably, longer incubation times as well as increasing thalidomide concentrations up to 100 µg/ml did not significantly induce cell death above controls (data not shown).

The potential of thalidomide to induce PCD in human embryonic fibroblasts (HEFs) was very similar to that in chicken embryonic cells (PLBCs, CEFs; FIG. 3C-E). The non-teratogenic thalidomide-derivative phthalimide did not induce PCD in PLBCs or HEFs (FIG. 3A-D).

HEFs were tested for differences in responses to the thalidomide enantiomers. In agreement with the results from chicken embryos, there were no differences in the potential of the two enantiomers to induce PCD in HEFs (FIG. 3F). Thus, primary embryonic cells of subsequent experiments were treated for six hours with racemic thalidomide at 10 µg/ml.

As in whole limb buds, thalidomide induced the expression of both, Bmp4 and Dkk1 in PLBCs and in HEFs but not in MEFs (FIG. 4A). Furthermore, phthalimide did not influence the expression of these genes in PLBCs and HEFs (data not shown). Interestingly, when thalidomide was applied to PLBCs either together with recombinant Noggin, an inhibitor of Bmp signaling (12), or together with an antibody against Dkk1, thalidomide-induced cell death was clearly reduced (FIG. 4B). Moreover, the simultaneous addition of Noggin and anti-Dkk1 antibody completely neutralized thalidomide-induced cell death (FIG. 4B). These results demonstrate that thalidomide acts via Bmps and Dkk1 to induce cell death in PLBCs.

In early limb development, Bmp4 activation leads to up-regulation of Dkk1 with subsequent inhibition of Wnt/β-catenin signaling and PCD. Both LiCl and (2Z,3E)-6-Bromoindirubin-3-oxime (BIO, Gsk3-Inhibitor IX) are Wnt signaling activators that operate downstream of Dkk1 and known to block Gsk3β activity, thereby preventing β-catenin phosphorylation and degradation. When applied to thalidomide-treated cells, both LiCl and Gsk3-Inhibitor IX were each able to completely abrogate thalidomide-induced cell death (FIG. 4B). These results demonstrate that thalidomide causes cell death in PLBCs by blocking Wnt/β-catenin signaling. Moreover, Noggin, anti-Dkk1 antibody and LiCl were each able to block thalidomide-induced cell death in CEFs (data not shown) and in HEFs (FIG. 4C). These data demonstrate that the effects of thalidomide on Bmp/Dkk1/Wnt signaling are not restricted to limb bud cells and that thalidomide affects the same signaling pathways in chicken and human embryonic cells.

Example 4

Thalidomide inhibits β-catenin activity.

Gsk3β participates in a number of signaling pathways. Therefore, additional experiments were performed to focus on the impact of thalidomide on canonical Wnt signaling. CEFs were transfected with a TOPflash reporter construct that contains Tcf/Lef binding sites and whose activity is a quantitative read-out for Wnt/β-catenin signaling. Treatment with Wnt3a-conditioned medium caused an induction of TOPflash activity, which was clearly counteracted by recombinant DKK1 (positive control) or thalidomide (FIG. 5A).

If cells are not exposed to a Wnt signal, β-catenin remains in the cytoplasm and becomes degraded. However, if a canonical Wnt signal is transmitted through Frizzled and low-density-lipoprotein-receptor-related-protein (LRP) receptors, stabilized β-catenin enters the nucleus and converts Tcf/Lef to a transcriptional activator. In CEFs and HEFs, β-catenin accumulated in the nucleus as a response to stimulation with Wnt3a (data not shown, FIG. 5B). Quantification revealed that β-catenin was predominantly localized in the nucleus in about 70% of the cells (FIG. 5B). However, treatment with thalidomide in the presence of Wnt3a caused a dramatic reduction in the number of CEFs and HEFs positive for nuclear β-catenin (data not shown, FIG. 5B). In HEFs, the number was reduced to 10% (FIG. 5B). Furthermore, transient expression of constitutively activated β-catenin counteracts thalidomide-induced cell death in CEFs and HEFs (FIG. 5C). These data demonstrate that thalidomide dramatically inhibits canonical Wnt/β-catenin signaling.

Example 5

Thalidomide-induced ROS formation is a prerequisite for enhanced Bmp expression and inhibition of Wnt signaling.

Thalidomide induces oxidative stress through the formation of ROS. The free-radical spin trapping agent Phenyl N-t-butylnitrone (PBN), which antagonizes oxidative stress, counteracts thalidomide-induced embryopathy. Thalidomide-induced cell death was completely inhibited by PBN in PLBCs (FIG. 6A). This demonstrates that thalidomide induces oxidative stress in the chicken model system.

Treatment with juglone, a potent inducer of ROS, provokes increased cell death in PLBCs (FIG. 6A). Juglone-induced cell death could be inhibited by PBN, Noggin, anti-Dkk1 antibody, LiCl and Gsk3-Inhibitor IX (FIG. 6A). Furthermore, counteracting oxidative stress through pre-treatment with PBN abolishes the up-regulation of Bmp4 and Dkk1 expression in thalidomide-treated PLBCs and HEFs (data not shown, FIG. 6B). These data illustrate that thalidomide initially causes oxidative stress leading to alterations of Bmp and subsequently of Wnt/β-catenin signaling.

The activation of β-catenin through the addition of Gsk3-Inhibitor IX or LiCl to BMP4-treated PLBCs counteracted BMP4-induced PCD in a dose-dependent manner (FIG. 6C). In contrast, treatment with PBN did not influence BMP4-induced PCD. These results demonstrate that Bmp signaling acts upstream of canonical Wnt signaling but downstream of ROS formation in thalidomide-induced molecular pathology responsible for PCD.

Example 6

Inhibition of Bmps, Dkk1 or Gsk3β counteracts thalidomide-induced teratogenicity.

Chicken embryos were treated with a combination of thalidomide and LiCl (0.6 mg per embryo) and TUNEL staining was performed on whole limb buds. Enhanced PCD was observed in 53% (42 of 79) of the individual limb buds isolated from thalidomide-treated HH stage 23/24 embryos. This number was reduced to 24% (19 of 80) when LiCl was applied to thalidomide-treated embryos at HH stages 17-19. This illustrates that the suppression of thalidomide-induced cell death by LiCl is an all-or-nothing rather than a gradual effect.

Embryos were next analyzed for embryopathy. Thalidomide treatment caused limb truncations in 19% of the embryos that survived to day seven of embryonic development. This number was reduced to 5% when Noggin (100 ng/embryo) or LiCl (0.6 mg/embryo) was applied at HH stages 17-19 to thalidomide-treated embryos (FIG. 7A). Inhibitor application at later stages (HH stages 22-24) did not prevent limb deformities (data not shown).

To determine whether enhanced Dkk1 expression is responsible for thalidomide-induced embryopathy, thalidomide-exposed HH stages 17-19 embryos were treated with a Dkk1 specific goat IgG. Limb truncations were found in 15% of the thalidomide-treated control embryos and in 3% of the embryos treated with both, thalidomide and anti-Dkk1 antibody (50 ng/embryo) (FIG. 7B).

Microphthalmia was observed in 23% of the thalidomide-treated control embryos. This number was reduced to 10% through the application of the Dkk1 antibody to thalidomide-treated embryos (FIG. 7C). In contrast, the application of 0.6 mg LiCl did not rescue thalidomide-induced microphthalmia.

However, increasing the dosage to 3.2 mg LiCl per embryo caused a reduction in the number of thalidomide-induced microphthalmia to 9% (FIG. 7D).

Although the inhibitors reduced the quantity of limb truncations and eye defects, they did not influence their spectrum of intensities. Thus, in agreement with the effect of the inhibitors on thalidomide-induced PCD in limb buds, the phenotypic rescue is an all-or-nothing effect. Importantly, no additional anomalies due to inhibitor-treatment were observed. In summary, these results demonstrate that the thalidomide-induced molecular pathologies responsible for limb truncations and microphthalmia are essentially identical.

REFERENCES

1. Hansen, J. M., and Harris, C. (2004) A novel hypothesis for thalidomide-induced limb teratogenesis: redox misregulation of the NF-kappaB pathway. *Antioxid. Redox Signal.* 6, 1-14.
2. Grotewold, L., and Rüther, U. (2002) The Wnt antagonist Dickkopf-1 is regulated by Bmp signaling and c-Jun and modulates programmed cell death. *EMBO J.* 21, 966-975.
3. Zuzarte-Luis, V., Montero, J. A., Rodriguez-Leon, J., Merino, R., Rodriguez-Rey, J. C., and Hurle, J. M. (2004) A new role for BMP5 during limb development acting through the synergic activation of Smad and MAPK pathways. *Dev. Biol.* 272, 39-52.
4. Maass, M., Gieffers, J., and Solbach, W. (2000) A therogenetically relevant cells support continuous growth of *Chlamydia pneumoniae. Herz* 25, 68-72.
5. Hagen, T., Sethi, J. K., Foxwell, N., and Vidal-Puig, A. (2004) Signaling activity of beta-catenin targeted to different subcellular compartments. *Biochem. J.* 379, 471-477.
6. Korinek, V., Barker, N., Morin, P. J., van Wichen, D., de Weger, R., Kinzler, K. W., Vogelstein, B., and Clevers, H. (1997) Constitutive transcriptional activation by a beta-catenin-Tcf complex in APC−/− colon carcinoma. *Science* 275, 1784-1787.
7. Qiang, Y. W., Endo, Y., Rubin, J. S., and Rudikoff, S. (2003) Wnt signaling in B-cell neoplasia. *Oncogene* 22, 1536-1545.
8. Yokouchi, Y., Sakiyama, J., Kameda, T., Iba, H., Suzuki, A., Ueno, N., and Kuroiwa, A. (1996) BMP-2/-4 mediate programmed cell death in chicken limb buds. *Development* 122, 3725-3734.
9. Pizette, S., and Niswander, L. (1999) BMPs negatively regulate structure and function of the limb apical ectodermal ridge. *Development* 126, 883-894.
10. Zimmerman, L. B., De Jesus-Escobar, J. M., and Harland, R. M. (1996) The Spemann organizer signal noggin binds and inactivates bone morphogenetic protein 4. *Cell* 86, 599-606.
11. Montero, J. A., Gañan, Y., Macias, D., Rodriguez-Leon, J. et al. (2001) Role of FGFs in the control of programmed cell death during limb development. *Development*, 128, 2075-2084.
12. Conlon, R. A. and Rossant, J. (1992) Exogenous retinoic acid rapidly induces anterior ectopic expression of murine Hox-2 genes in vivo. *Development*, 116, 357-368.

All references cited in this specification are hereby incorporated by reference in their entirety. The discussion of the references herein is intended merely to summarize the assertions made by their authors and no admission is made that any reference constitutes prior art relevant to patentability. Applicant reserves the right to challenge the accuracy and pertinence of the cited references.

As various changes could be made in the above methods and compositions without departing from the scope of the invention, it is intended that all matter contained in the above description be interpreted as illustrative and not in a limiting sense. Unless explicitly stated to recite activities that have been done (i.e., using the past tense), illustrations and examples are not intended to be a representation that given embodiments of this invention have, or have not, been performed.

TABLE I

Table I. Thalidomide induces variable limb truncations in chicken embryos. Note that in the upper part of the table total embryos and in the lower part individual limbs were counted. Left and right wings/hindlimbs were likewise affected. Other limb malformations, such as fusion at the level of the metacarpal cartilage and abducted legs, were also observed, observed, but at a much lower frequency (in total 4%, data not shown). st, stylopod; z, zeugopod; a, autopod; m, missing; t, truncated; n, normal.

|  | forelimb | hindlimb | both | total |
|---|---|---|---|---|
| unilateral | 17 | 7 | 2 | 26 |
| bilateral | 6 | 15 | — | 21 |
| total | 23 | 22 | 2 | 47 |

| st | z | a | forelimb | hindlimb | total |
|---|---|---|---|---|---|
| m | m | m | 4 | 21 | 25 |
| t | m | m | 25 | 3 | 28 |
| t | t | m | 2 | 11 | 13 |
| n | t | m | — | 4 | 4 |

TABLE II

Table II. Thalidomide induces variable micophthalmia in chicken embryos. Numbers of embryos with eye defects as indicated are given. Note that in the cases of unilateral microphthalmia the right eye was more frequently affect (37 embryos) than the left one.

|  | severe | mild | total |
|---|---|---|---|
| unilateral | 33 | 15 | 48 |
| bilateral | 16 | 1 | 17 |
| total | 49 | 16 | 65 |

What is claimed is:

1. A method of inhibiting the teratogenicity of an anti-neoplastic agent, the method comprising administering a pharmaceutical composition comprising Noggin.
2. A method of inhibiting the teratogenicity of an anti-neoplastic agent, the method comprising administering a pharmaceutical composition comprising an anti-Dkk1 antibody.
3. A method of inhibiting the teratogenicity of an anti-neoplastic agent, the method comprising administering a pharmaceutical composition comprising LiCl or Gsk3-Inhibitor IX.
4. The method of claim 1, wherein the anti-neoplastic agent is thalidomide or lenalidomide.
5. The method of claim 2, wherein the anti-neoplastic agent is thalidomide or lenalidomide.
6. The method of claim 3, wherein the anti-neoplastic agent is thalidomide or lenalidomide.
7. The method of claim 1, further comprising administering a pharmaceutical composition comprising an anti-Dkk1 antibody.
8. The method of claim 2, further comprising administering a pharmaceutical composition comprising Noggin.

* * * * *